United States Patent [19]

Podos et al.

[11] 4,343,794

[45] Aug. 10, 1982

[54] METHOD OF REDUCING INTRAOCULAR PRESSURE WITH SALTS OF VANADIC ACID

[75] Inventors: Steven Podos, New York, N.Y.; Theodore Krupin, Creve Coeur; Bernard Becker, University City, both of Mo.

[73] Assignees: Mt. Sinai, New York, N.Y.; Washington University, St. Louis, Mo.

[21] Appl. No.: 147,172

[22] Filed: May 6, 1980

[51] Int. Cl.³ .................... A61K 33/24; A61K 31/28
[52] U.S. Cl. .................................. 424/131; 424/287
[58] Field of Search ............................. 424/131, 287

[56] References Cited
PUBLICATIONS

Brit. J. Ophthol. 45,202 (1961)–Cole.
Biochem. 16:4572, 1977–Josephson et al.
Nature 272:551, 1978–Beauge et al.
Biochem. Biophys. Acta 291:680, 1973–Perrone et al.
Invest Ophthalmol. 2:325, 1963–Becker.
A.M.A. Arch. Ophthal. 68:227, 1962–Simon et al.
Am. Chem. Soc., 18:325, 1979–Bond et al.
Invest. Ophthalmol. 3:523, 1964–Bonting et al.
Nature 7:552, 1978–Cantley et al.
J. Am. Chem. Soc. 100:5210–5212, 1978, Cantley et al.
Analyt. Biochem. 78:252, 1977–Ferrendelli et al.
Life Sci. 18:529, 1976–Frandsen et al.
Invest. Ophthalmol. 13:455, 1974–Gausterland et al.
Exp. Eye Res. 5:208–220, 1966–Jones et al.
Nature 281:337, 1979, Simon.
J. Biol. Chem. 247:1106, 1972–Steinev et al.
J. Biol. Chem. 252:7421, 1977–Cantley et al.
AMA Arch. Ophthalmol. 68:227, 1962–Simon et al.
Life Sci. 18:529, 1976–Frandsen et al.
Proc. Natl. Acad. Sci., U.S.A. 76:2620–2624, 1979, ARVO, 1980.
Analyt. Biochem. 58:541, (1974)–Salomon et al.
J. Biol. Chem. 247:1106, 1972–Steinev et al.
Exp. Eye Res. 27:387–397, (1978)–Neufeld.

Primary Examiner—Douglas W. Robinson
Attorney, Agent, or Firm—Brumbaugh, Graves, Donohue & Raymond

[57] ABSTRACT

This invention relates to a method of reducing intraocular pressure in mammals which comprises administering topically to the eye a vanadium compound in an amount effective to reduce intraocular pressure.

6 Claims, No Drawings

METHOD OF REDUCING INTRAOCULAR PRESSURE WITH SALTS OF VANADIC ACID

This invention relates to a method of lowering intraocular pressure and treating glaucoma in mammals using vanadium compounds and particularly to the topical application of salts of vanadic acid (vanadates) to the eye of mammals in order to lower the intraocular pressure caused by glaucoma.

Glaucoma refers to a group of diseases of the eye which are characterized by abnormally high intraocular pressure. The outer shell of the eyeball is made up of three coats. A tough outer fibrous tunic composed of variously arranged connective tissue fibers, the uveal tunic and the retina. The choroid is the posterior segment of the uveal tunic. The anterior part of the uvea, in part, is referred to as the ciliary body and is lined with two epithelial cell layers which secrete the aqueous humor which fills the anterior chamber of the eye. In a healthy eye the humor flows from the ciliary body through the pupil into the anterior chamber of the eye and leaves the eye through Schlemm's canal. The rate of formation and exit of this aqueous humor determines the intraocular pressure in the eyeball.

In subjects suffering from glaucoma the rate of elimination of aqueous humor from the eye is reduced which results in fluid build up within the eye and increased intraocular pressure. If high intraocular pressure is allowed to continue untreated it interferes with the blood supply to the nerve fibers of the retina and optic nerve and if left uncorrected the optic nerve dies and blindness results.

Glaucoma can be treated both through surgery or drugs. Surgery seeks to create new outlets for the aqueous humor and thereby reduces the intraocular pressure. A number of drugs have been discovered which when either taken internally or applied topically to the eye lower intraocular pressure but many are toxic and cause undesirable side effects. Drugs such as pilocarpine, epinephrine, acetazalamide, timolol, and ouabain have been used to lower intraocular pressure and/or treat glaucoma.

The mechanism by which epinephrine lowers intraocular pressure is not fully understood but some believed it to be linked to an increase of adenylate cyclase and a corresponding increase in adnosine 3',5' cyclic monophosphate (cyclic-AMP). Adenylate cyclase is an enzyme which converts adenosine triphosphate (ATP) into cyclic-AMP. Neufeld, A. H., "Influence of Cyclic Nucleotides on Outflow Facility In the Vervet Monkey", *Exp. Eye Res.*, 27:387, 1978, reported that an elevation of cyclic-AMP in rabbits' eyes was related to an increased outflow of humor and a resulting decrease in intraocular pressure. He also reported that intraocular administration of cyclic-AMP decreased intraocular pressure and increased the outflow of the aqueous humor in rabbits and Vervet monkeys.

It has been demonstrated that when ouabain is injected into the vitreous of the eye, ($Na^+, K^+$) ATPase (adenosine triphosphatase) is inhibited and intraocular pressure is lowered, Simon, K. A., Bonting, S. L. and Hawkins, N. M.: "Studies on Sodium-Potassium Activated Adenosine Triphosphatase, II. Formation of Aqueous Humor", *Exp. Eye Res.*, 1:253, 1962. ATPase is an enzyme which is postulated to play a role in the production of aqueous humor, Bonting, S. L., Simon, K. A., and Hawkins, N. M.: "Studies on Sodium-Potassium Activated Adenosine Triphosphatase, I. Quantitative Distribution in Several Tissues of the Cat", *Arch. Biochem.*, 95:416, 1961. It is believed that the observed decrease in intraocular pressure after ouabain injections is somehow related to the inhibition of ($Na^+, K^+$) ATPase.

Vanadates, that is salts of vanadic acid, are known from in vitro experiments to inhibit various ATPase enzymes. Cantley, L. C. et al. "Vanadate is a Potent ($Na^+, K^+$) ATPase Inhibition Found in ATP Derived from Muscles", *J. Biol. Chem.*, 252:7421, 1977; Goodno, C. C.: "Inhibition of Myosin ATPase by Vanadate Ion", *Proc. Natl. Acad. Sci., U.S.A.*, 76:2620-2624, 1979; Josephson, L. and Cantley, L. C.: "Isolation of a Potent (Na-K) ATPase Inhibitor From Striated Muscle", *Biochem.*, 16:4572, 1977; Kobayashi, T., Martensen, T., Nath, J. and Flavin, M.: "Inhibition of Dynein Cytoplasmic Motility", *Biochem. Biophys. Res. Comm.*, 81:1313-18, 1978. Cantley, L. C., et al. in "Vanadate Inhibits the Red Cell ($Na^+, K^+$) ATPase From the Cytoplasmic Side", *Nature*, 272:552, 1978, have also demonstrated that vanadates are transported across the cell membrane into the cytoplasm and inhibit ($Na^+, K^+$) ATPase by action from within the cell. Vanadate was also known to induce formation of adenylate cyclase and the production of cyclic-AMP in membranes isolated from rat fat cells. Schwabe, U., Puchstein, Hannemann, H. and Sochtig, E.: "Activation of Adenylate Cyclase by Vanadate", *Nature*, 277:143, 1979.

It was the object of this invention to find a method of lowering intraocular pressure in mammals using topical applications of vanadium compounds. It has now been found that vanadium compounds can be applied topically to the eyes of mammals to lower intraocular pressure and to treat glaucoma.

Salts of vanadic acid, sometimes referred to herein as vanadates, occur in ortho ($M_3VO_4$), meta ($MVO_3$) and pyro ($M_4V_2O_7$) forms. Sodium metavanadate and sodium orthovanadate have been tested in rabbits and monkeys and are known to be effective in lowering intraocular pressure. It is believed, however, that vanadium, any pharmaceutically acceptable salt of vanadic acid, particularly sodium, magnesium and potassium or other pharmaceutically acceptable vanadium compounds in which the vanadium has a valence of from 2 to 5, would also be effective, for example vanadium mono-oxide (VO), vanadium sesqui oxide ($V_2O_3$), vanadium dioxide ($VO_2$), vanadium pentaoxide ($V_2O_5$) and vanadium oxy, di and tri halides, vanadium nitride, vanadium carbide, vanadium halides, vanadium sulfate, vanadium nitrate, vanadium salts of organic acids such as vanadium acetate and vanadium chelates.

The vanadium compound can be applied topically to the eye in any pharmaceutically accepted manner including but not limited to sterile opthalmic solutions, ointments, subconjunctival injections, and slow release devices. In addition to the active vanadium compound, the pharmaceutical composition can contain among other things pharmaceutically acceptable preservatives, anti oxidants, viscosity vehicles, stabilizers and buffers.

Vanadate salts were tested in male albino rabbits and male rhesus monkeys by applying freshly prepared water solutions containing from about 0.01% to 2.0% by weight sodium metavanadate or sodium orthovanadate at about pH 7.0-8.0 to one of the animal's eyes and a control solution to the other eye. The effect of the vanadate solutions was determined by measuring the intraocular pressure, episcleral venous pressure, as well as the ascorbate concentration and cyclic-AMP concentration of the posterior and anterior aqueous fluids of the eye. Both sodium orthovanadate and metavanadate significantly lowered intraocular pressure in the rabbits and monkeys.

The invention will be more clearly understood by reference to the following examples which are given by way of illustration and are not meant to limit this invention in any way.

EXAMPLE 1

Vanadate solutions containing 0.3%, 0.5%, 1.0% and 2.0% by weight sodium orthovanadate ($Na_3VO_4$) obtained from Sigma Chemical Co. were prepared in distilled water just prior to topical ocular delivery. The solutions were adjusted to a pH between 7.0 and 8.0 with one normal hydrochloric acid.

Eight unanesthetized male albino rabbits (1.5 to 2.5 kg) were restrained in a cloth wrap and 0.05 ml of the 0.3% solution was applied to one eye of each of the rabbits. The aqueous diluent was administered to the fellow eye of each rabbit as a control. The procedure was repeated for the 0.5%, 1.0% and 2.0% solutions.

Intraocular pressure was measured with a manometrically calibrated pneumotonograph using topical 0.5% proparacaine hydrochloride as the anesthetic agent. Tonography was performed with an Alcon EDT-103 tonography unit using the same topical anesthetic agent. Episcleral venous pressure was determined with a 3 mm applanating head attached to a force displacement transducer and mounted on a Haag-Streit biomicroscope. Podos, S. M., Minas, T. F., and Macri, F. J.: "A New Instrument To Measure Episcleral Venous Pressure, Comparison on Normal Eyes and Eyes with Primary Open-Angle Glaucoma", *Arch. Ophthalmol.*, 80:209, 1968. Aqueous humor flow (F) was estimated from the tonographic data using the equation $F=(P_o-P_v)C$, where $P_o$ was the intraocular pressure (mm Hg), $P_v$ the episcleral venous pressure (mm Hg), and C the outflow facility (μl/min/mm Hg).

Two hours after topical therapy with 0.5% $Na_3VO_4$ or its diluent, paracentesis of the posterior and anterior chambers were performed in both the test and control rabbits after topical anesthesia with 0.5% proparacaine hydrochloride. Ascorbate levels in the eye were estimated by microtitration and protein concentration was determined with Folin phenol reagent. Becker, B.: "The Effect of the Carbonic Anhydrase Inhibitor, Acetazolamide, On The Composition of the Aqueous Humor", *Am. J. Ophthalmol.*, 40 (Part II): 129, 1955 and Lowry, O. H., Rosenbrough, N. J., Farr, A. L., and Randall, R. J.: "Protein Measurement with the Folin Phenol Reagent", *J. Biol. Chem.*, 192:265, 1951. The Kinsey-Palm formula for the ratio of aqueous humor flow coefficient ($k_{fa}$) to the diffusion coefficient ($k_{dpa}$) for ascorbate was used to determine the effects of topical administration of vanadate on this ratio. Kinsey, V. E. and Palm, E.: "Posterior and Anterior Chamber Aqueous Humor Formation", *A.M.A. Arch. Ophthalmol.*, 53:330, in cold 10% tricholoracetic acid. The samples were acetylated, and cyclic-AMP was measured by radioimmunoassay.

Statistical analysis employed the paired t-test when comparing treated and diluent control eyes. The Student t-test was used to compare the responses in different groups of rabbits. The results of these tests are shown in Tables I and III.

EXAMPLE 2

Vanadate solutions containing 1.0% and 2.0% sodium metavanadate ($NaVO_3$) obtained commercially in Europe were prepared and tested as in Example 1 using 8 rabbits for testing the 2.0% solution and 10 rabbits for the 1.0% solution. The results of these tests are shown in Table II.

Results

Topical administration of $NaVO_3$ (Table I) or $Na_3VO_4$ (Table II) to rabbit eyes resulted in reductions of intraocular pressure related to the dose administered. The mean intraocular pressure was significantly lower after sixty minutes in eyes treated with $NaVO_3$) (1% or 2%) or $Na_3VO_4$ (0.3%, 0.5%, 1.0% or 2.0%) and the reductions persisted for at least 240 minutes. The decrease in intraocular pressure was similar (Student t-test, $p>0.2$) during the 240 minutes following 0.5%, 1% and 2% $Na_3VO_4$ or 1% and 2% $NaVO_3$. Ocular irritation occurred only following the administration of the 2% solutions but even at this concentration, slit-lamp examination showed no cells or flare in the anterior chamber of the treated eye.

Tonography after the random unilateral administration of 1% vanadate confirmed the reduction of intraocular pressure in twelve rabbits. Intraocular pressure in the treated eye (15.8±1.0 Hg mean±SEM) was significantly ($p<0.025$) lower than the control eye (18.5 0.5 mm Hg). Outflow facility was similar ($p>0.5$) in vanadate treated eyes (0.28±0.02 μl/min/mm Hg) and control diluent treated eyes (0.29±0.02 μl/min/mm Hg). The average baseline episcleral venous pressure (12.0±0.3 mm Hg) was not altered significantly ($p>0.1$) two hours after vanadate administration (11.1 0.5 mm Hg). Using the equation $F=(P_o-P_v)C$, aqueous humor flow average, 1.9 μl/min in control eyes and 1.3 μl/min in vanadate treated eyes. This represented a mean decrease two hours after topical administration of 1% vanadate of approximately 30%.

Anterior chamber aqueous humor ascorbate concentration (Table III) were symmetrical two hours after unilateral topical administration of 0.5% $Na_3VO_4$ in nine rabbits which showed a significant decrease in intraocular pressure (17.0±0.9 mm Hg vs 12.6±0.7 mm Hg). However, posterior chamber aqueous ascorbate was significantly ($p<0.01$) higher in the $Na_3VO_4$ treated eyes. The increased posterior chamber ascorbate was compatible with a decreased entry of water in the posterior chamber. Since the new anterior chamber steady-state value for ascorbate may not have been reached at this time, the change in $k_{fa}/k_{dpa}$ could only be approximated at about 40%.

Mean aqueous humor protein was not significantly ($p>0.7$) different in the eyes treated with 0.5% $Na_3VO_4$ in comparison to the fellow diluent-treated eyes (Table III). Anterior chamber aqueous humor cyclic-AMP was not significantly ($p>0.7$) altered two hours after unilaterial administration of 0.5% $Na_3VO_4$ (Table III).

The results from Examples 1 and 2 demonstrate a lowering of intraocular pressure in rabbits following the topical administration of vanadate as $NaVO_3$ or $Na_3VO_4$. The reduction in intraocular pressure persists for at least 360 minutes and there appears to be no effect on the opposite eye. Systemic drug absorption and a systemic action do not appear to be significant factors in the decreased intraocular pressure. The reduction in intraocular pressure is not associated with significant changes in outflow facility or episcleral venous pressure, and is believed to be largely due to an effect on aqueous humor production. Both the tonographic and aqueous humor ascorbate data in rabbits are compatible with this conclusion.

EXAMPLE 3

Five male rhesus monkeys (3.5 to 4.5 kg) were treated as in Example 1 using 0.5% sodium orthovanadate. Each monkey was given ketamine hydrochloride catalepsia, 12 mg/kg intramuscularly. A similar lowering of intraocular pressure as observed in Example 1 for rabbits occurs unilaterally in the topically treated normal monkey eyes.

The baseline intraocular pressure in five monkeys was $17.4 \pm 1.0$ mm Hg in the experimental eyes and $17.9 \pm 1.0$ mm Hg in the control eyes. Intraocular pressure was significantly ($p < 0.01$) reduced, one, two and three hours following topical delivery of 0.5% $Na_3VO_4$. After three hours the mean intraocular pressure was $12.6 \pm 1.0$ in the vanadate treated eyes and $17.4 \pm 1.1$ in the diluent-treated fellow control eyes.

TABLE I
Effect Of Sodium Orthovanadate ($Na_3 VO_4$) On Intraocular Pressure In Rabbits

| Concentration | No. | Mean Intraocular Pressure (mm Hg) $\pm$ SEM | | | |
|---|---|---|---|---|---|
| | | 0 Min | 60 Min | 120 Min | 240 Min |
| 2.0% | 8 | $16.5 \pm 1.1$ | $12.1 \pm 0.3$** | $12.5 \pm 0.5$** | $14.5 \pm 0.7$*** |
| Diluent | 8 | $16.5 \pm 1.1$ | $16.0 \pm 1.0$ | $16.2 \pm 1.1$ | $16.0 \pm 0.9$ |
| 1.0% | 8 | $17.2 \pm 1.2$ | $13.1 \pm 1.1$** | $12.8 \pm 0.7$** | $13.0 \pm 0.5$** |
| Diluent | 8 | $16.6 \pm 1.1$ | $17.0 \pm 1.0$ | $18.2 \pm 1.1$ | $17.0 \pm 1.0$ |
| 0.5% | 8 | $17.0 \pm 0.9$ | $12.2 \pm 0.7$* | $12.3 \pm 0.7$* | $13.5 \pm 0.7$*** |
| Diluent | 8 | $16.5 \pm 0.8$ | $16.7 \pm 0.6$ | $16.8 \pm 0.9$ | $16.3 \pm 0.4$ |
| 0.3% | 8 | $18.8 \pm 0.6$ | $15.6 \pm 0.7$** | $15.4 \pm 0.7$** | $17.4 \pm 0.5$ |
| Diluent | 8 | $18.6 \pm 0.5$ | $18.6 \pm 0.6$ | $18.2 \pm 0.4$ | $18.4 \pm 0.7$ |

Significant difference between eye treated with $Na_3 VO_4$ and fellow diluent-treated control eye, paired t-test
*$p < 0.001$
**$p < 0.005$
***$p < 0.01$

TABLE II
Effect of Sodium Metavanadate ($Na VO_3$) On Intraocular Pressure In Rabbits

| Concentration | No. | Mean Intraocular Pressure (mm Hg) $\pm$ SEM | | | | |
|---|---|---|---|---|---|---|
| | | 0 Min | 60 Min | 120 Min | 240 Min | 360 Min |
| 2.0% | 8 | $20.5 \pm 1.1$ | $14.5 \pm 0.8$* | $13.6 \pm 0.6$* | $16.9 \pm 1.1$* | $17.1 \pm 0.8$* |
| Diluent | 8 | $19.9 \pm 1.0$ | $19.0 \pm 0.6$ | $19.0 \pm 0.6$ | $19.8 \pm 1.0$ | $19.2 \pm 1.1$ |
| 1.0% | 16 | $23.0 \pm 0.5$ | $16.9 \pm 0.6$* | $17.2 \pm 0.6$* | $17.0 \pm 0.7$* | $19.2 \pm 0.6$* |
| Diluent | 16 | $22.2 \pm 0.4$ | $22.3 \pm 0.7$ | $23.1 \pm$ | $22.4 \pm 0.8$ | $22.9 \pm 0.7$ |

*Significant difference between eye treated with $Na VO_3$ abd fellow diluent-treated control eye, paired t-test, $p < 0.005$.

TABLE III
Effect Of Sodium Orthovanadate ($Na_3 VO_4$) On Aqueous Humor Ascorbate, Protein, and Cyclic AMP in Nine Rabbits*

| Con-centration | Ascorbate (mg/dl $\pm$ SEM) | | Protein (mg/dl $\pm$ SEM) | Cyclic AMP (nM $\pm$ SEM) |
|---|---|---|---|---|
| | Anterior Chamber | Posterior Chamber | Anterior Chamber | Anterior Chamber |
| 0.5% | $25.5 \pm 2.0$ | $41.1 \pm 2.3$+ | $0.72 \pm 0.13$ | $0.57 \pm 0.07$ |
| Diluent | $25.0 \pm 1.9$ | $34.0 \pm 3.0$ | $0.68 \pm 0.08$ | $0.52 \pm 0.09$ |

*Aqueous humor obtained two hours after topical $Na_3 VO_4$
+Significant difference between eye treated with $Na_3 VO_4$ and fellow diluent-treated control eye, paired t-test $p < 0.01$.

We claim:

1. A method of reducing intraocular pressure in mammals which comprises applying topically to the eye a salt of vanadic acid, in which the vanadium has a valence of from 3 to 5, in an amount effective to reduce intraocular pressure.

2. A method of reducing intraocular pressure as described in claim 1 wherein the salt of vanadic acid is selected from the group consisting of sodium orthovanadate, potassium orthovanadate, magnesium orthovanadate, sodium metavanadate, potassium metavanadate and magnesium metavanadate.

3. A method of reducing intraocular pressure as described in claim 2 wherein the salt of vanadic acid is selected from the group consisting of sodium orthovanadate and sodium metavanadate and is applied topically as a solution containing about 0.01-2% by weight.

4. A method of treating glaucoma in mammals which comprises applying topically to the eye a salt of vanadic acid, in which the vanadium has a valence of from 3 to 5, in an amount effective to reduce intraocular pressure.

5. A method of treating glaucoma as described in claim 4 wherein the salt of vanadic acid is selected from the group consisting of sodium orthovanadate, potassium orthovanadate, magnesium orthovanadate, sodium metavanadate, potassium metavanadate and magnesium metavanadate.

6. A method of treating glaucoma as described in claim 5 wherein the vanadate is applied topically as a solution containing about 0.01-2% by weight sodium orthovanadate.

* * * * *

UNITED STATES PATENT AND TRADEMARK OFFICE
CERTIFICATE OF CORRECTION

PATENT NO. : 4,343,794

DATED : August 10, 1982

INVENTOR(S) : Podos, et al.

It is certified that error appears in the above—identified patent and that said Letters Patent is hereby corrected as shown below:

First page, Item 73, "Mt. Sinai" should be --Mt. Sinai School of Medicine of the City University of New York--;

Col. 5, second line of Table II, "Intracular" should be --Intraocular--;

Col. 5, third line of Table II, "Intracular" should be --Intraocular--;

Col. 5, penultimate line of Table II, "abd" should be --and--.

Signed and Sealed this

Sixth Day of December 1983

[SEAL]

Attest:

Attesting Officer

GERALD J. MOSSINGHOFF

Commissioner of Patents and Trademarks